United States Patent [19]

Davis et al.

[11] 4,348,544
[45] Sep. 7, 1982

[54] RECOVERY OF PROPANE FROM HF ALKYLATION VENT GAS

[75] Inventors: Edgar D. Davis; David J. Cones, both of Borger, Tex.

[73] Assignee: Phillips Petroleum Company, Bartlesville, Okla.

[21] Appl. No.: 75,393

[22] Filed: Sep. 14, 1979

[51] Int. Cl.³ .......................... C07C 7/00; C07C 2/56
[52] U.S. Cl. ................................. 585/300; 585/719; 585/723
[58] Field of Search ....................... 585/719, 723, 800

[56] References Cited

U.S. PATENT DOCUMENTS 2,542,927  2/1951  Kelley ............................. 585/331
2,929,857  3/1960  Hutto ............................. 585/701
3,206,390  9/1965  Van Pool ......................... 585/719
4,009,221  2/1977  Carter ............................ 585/711

Primary Examiner—Curtis R. Davis

[57] ABSTRACT

Vent gases containing propane and HF obtained from a hydrocarbon alkylation operation are treated together with an alkylate either before or after it has been debutanized thus to remove HF from said vent gases and/or the vent gases are combined with a normal butane stream before it is treated to remove HF therefrom thus to remove HF from said vent gases. In any event described, the propane in the vent gases is advantageously recovered in the normal butane containing stream.

4 Claims, 3 Drawing Figures

RECOVERY OF PROPANE FROM HF ALKYLATION VENT GAS

BRIEF SUMMARY OF THE INVENTION

Improved recovery of propane, and of HF, from vent gases resulting from an alkylation of hydrocarbons as in the alkylation of an isoparaffin with an olefin in the presence of HF catalyst, is effected by admixing the vent gases with a stream obtained in fractionation ultimately to produce an alkylate product prior to treatment of said stream to remove HF therefrom and to produce a normal butane-containing stream, whereby propane in said vent gases is recovered in said normal butane containing stream.

DETAILED DESCRIPTION

Figure 1:
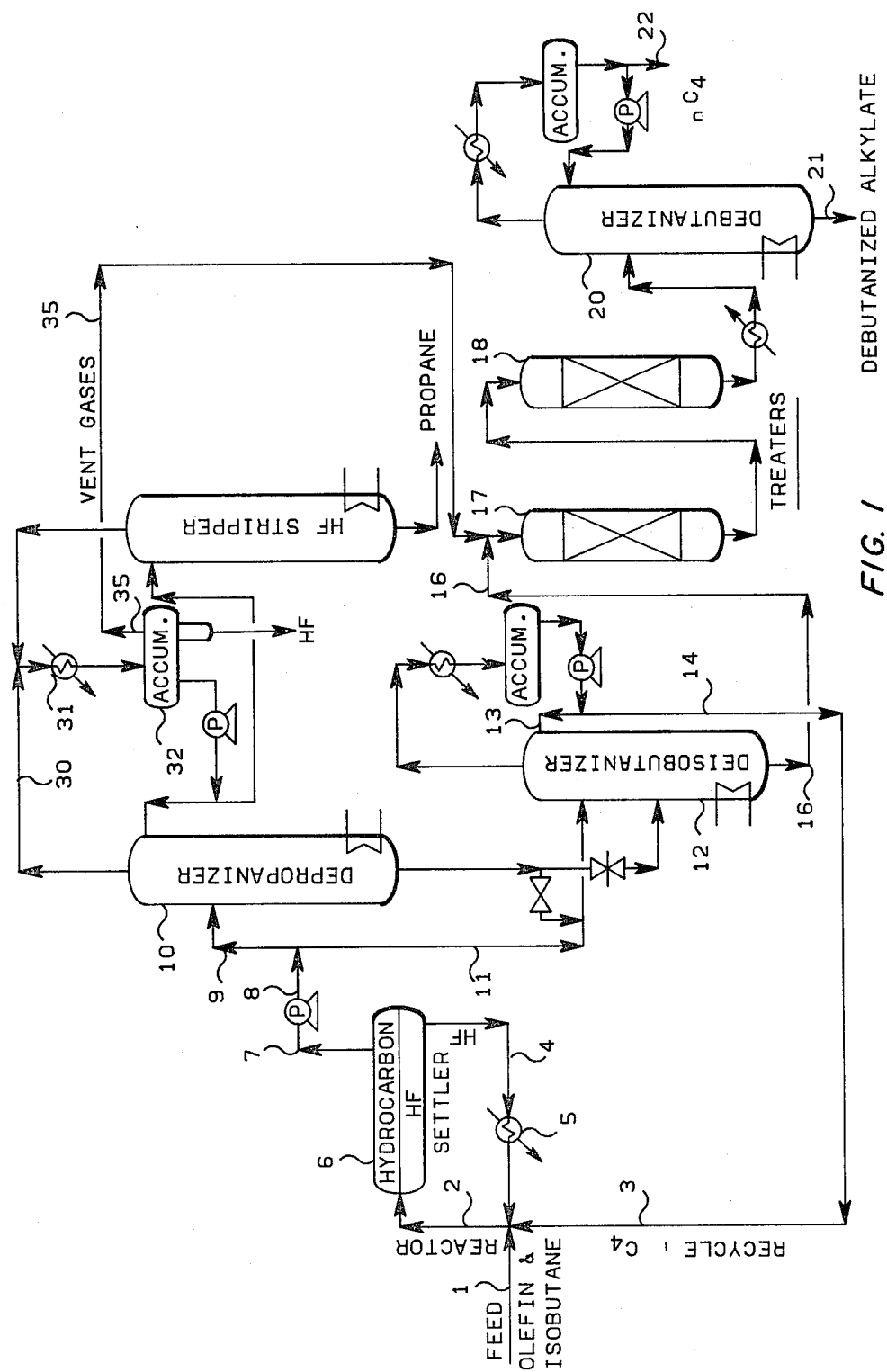
In FIG. 1 there is shown an operation according to the invention in which vent gases are combined with an alkylate prior to treatment of the same to remove HF therefrom.

This invention relates to alkylation. In one of its aspects the invention relates to the alkylation of hydrocarbons to produce an alkylate-containing stream. In another of its aspects, the invention relates to the production of alkylate hydrocarbon from an alkylate-containing hydrocarbon stream obtained as effluent from an alkylation of hydrocarbons, e.g., an isoparaffin with an olefin, in the presence of HF catalyst wherein an improved recovery of propane and HF from vent gases produced in the process are effected.

In one of its concepts, the invention provides a process wherein a hydrocarbon phase resulting from a settler in a conventional HF-Alkylation operation is fractionated to depropanize the same, generating vent gases containing propane and HF, the depropanized hydrocarbon is fractionated to produce an alkylate product stream containing normal butane, the vent gases are mixed with said stream prior to treatment of said stream to remove HF therefrom, resulting in a normal butane containing stream containing said propane from which HF has been removed in said treatment. In another concept of the invention, it provides a process, as further described herein, wherein a portion of alkylation effluent is depropanized obtaining vent gases containing propane and HF, another portion of said alkylation effluent is deisobutanized to produce an alkylate-containing stream also containing normal butane, the vent gases containing propane and HF are then admixed with said last-mentioned stream prior to treatment to remove HF therefrom following which the treated stream is debutanized to produce a stream of normal butane containing the propane of the vent gases and a debutanized alkylate is produced. In a further concept of the invention, the hydrocarbon phase from the settler is passed to a conventional isostripper from which vent gases are obtained overhead, the gas containing HF and propane, there is removed a side stream containing normal butane to which the vent gases are added and upon said addition the stream is treated to produce a normal butane containing stream also containing the propane. An alkylate containing stream is removed from the isostripper separately. In a still further concept of the invention, vent gases are obtained from the isostripper, as above described, an alkylate and normal butane containing stream is also removed from the isostripper, the vent gases are admixed with said last-mentioned stream, the admixed gases and stream are treated to remove HF therefrom following which the treated stream is debutanized to produce normal butane containing propane which was in the vent gases and an alkylate containing stream.

In view of energy producing material shortages, e.g., petroleum oil, it is important to most efficiently recover, with least expenditure of energy, a maximum amount of propane which may be in vent gases. Further, from an ecological point of view it is important to remove HF from any vent gases also with smallest expenditure of energy.

Energy is required in the beneficiation of minerals with which to produce metals, etc., needed in the construction of equipment for treating, e.g., fractionating streams obtained in petroleum refining or conversion operations. As related to the present invention, it is important to treat vent gases obtained from an alkylation, as herein described, and to do so with minimum expenditure of energy for the treatment and in the production of operation of equipment with which to effect such treatment.

It is an object of the present invention to provide an improved process for the recovery of propane from vent gases obtained in fractionation of an alkylate-containing effluent produced in alkylation of hydrocarbons in the presence of HF catalyst. It is another object of the invention to recover in improved manner, HF from such vent gases. It is a further object of the invention to provide an improved process for the fractionation of an alkylation effluent to remove vent gases therefrom and to recover, variously, propane and HF from said vent gases making use of existing equipment.

Other aspects, concepts, objects and the several advantages of the invention are apparent from a study of the drawings and the appended claims to the invention.

According to the present invention, there is provided, generally speaking, a process in which vent gases derived from a hydrocarbon alkylation, as herein described, are combined during fractionation to produce ultimately a normal butane containing stream containing the propane from said vent gases, the normal butane being obtained substantially free from the HF together with which the propane was present in said vent gases.

From the foregoing description of that which follows, it can be seen that the invention eliminates separate treating, e.g., caustic wash of vent gases and also that it recovers valuable propane yielded in the normal butane, for example, in a liquified petroleum gas.

FIG. 1 shows charging an HF alkylation hydrocarbon phase in part to a depropanizer (in an amount to rid the system of propane added in the fresh feed and produced in the alkylation) and in part to a deisobutanizer. Vent gases (HF, propane) from the depropanizer overhead accumulator are passed to the treater used to treat HF from the deisobutanized alkylate (normal butane and heavier) recovered from the bottom of the deisobutanizer. The treated admixture is then debutanized to recover debutanized alkylate and normal butane containing the propane which was in the vent gases.

Figure 2:
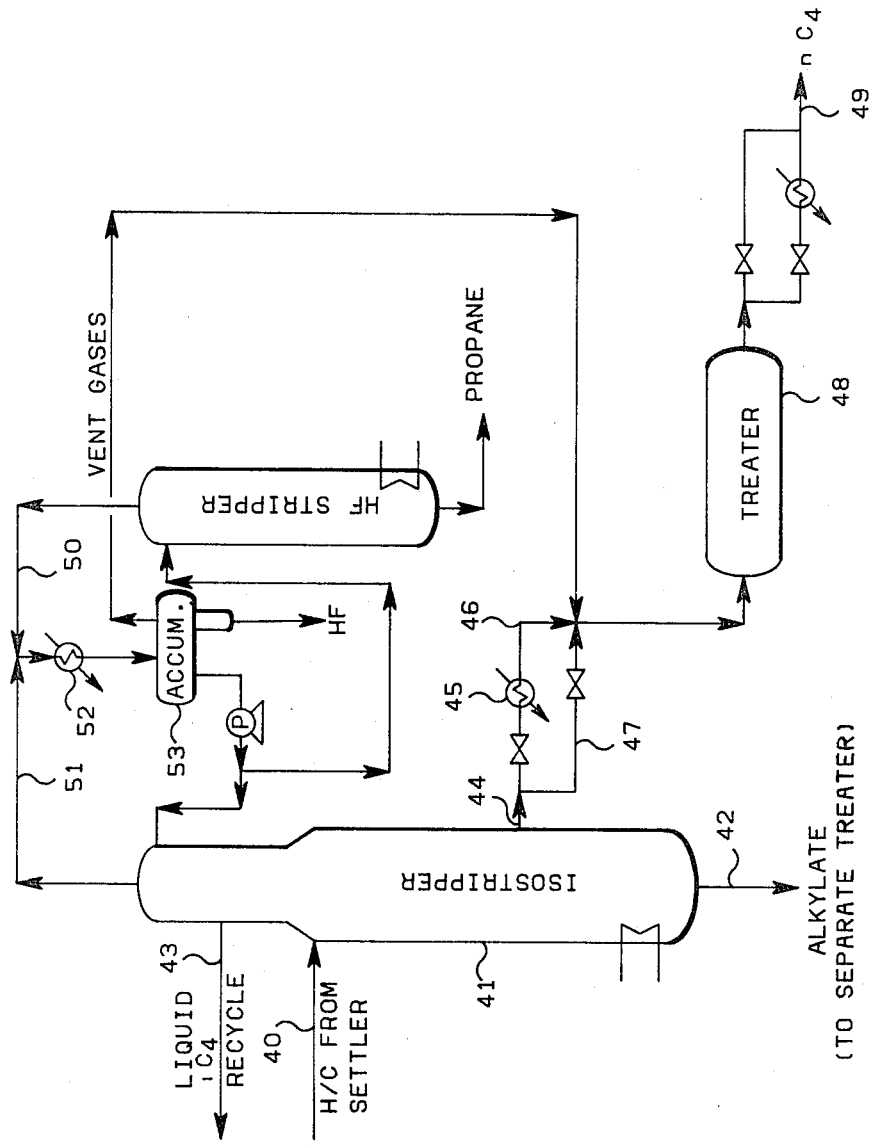
In FIG. 2, there is shown a treatment of vent gases by combining the same with a normal butane side stream from an isostripper prior to treating said side stream to remove HF therefrom.
Figure 3:
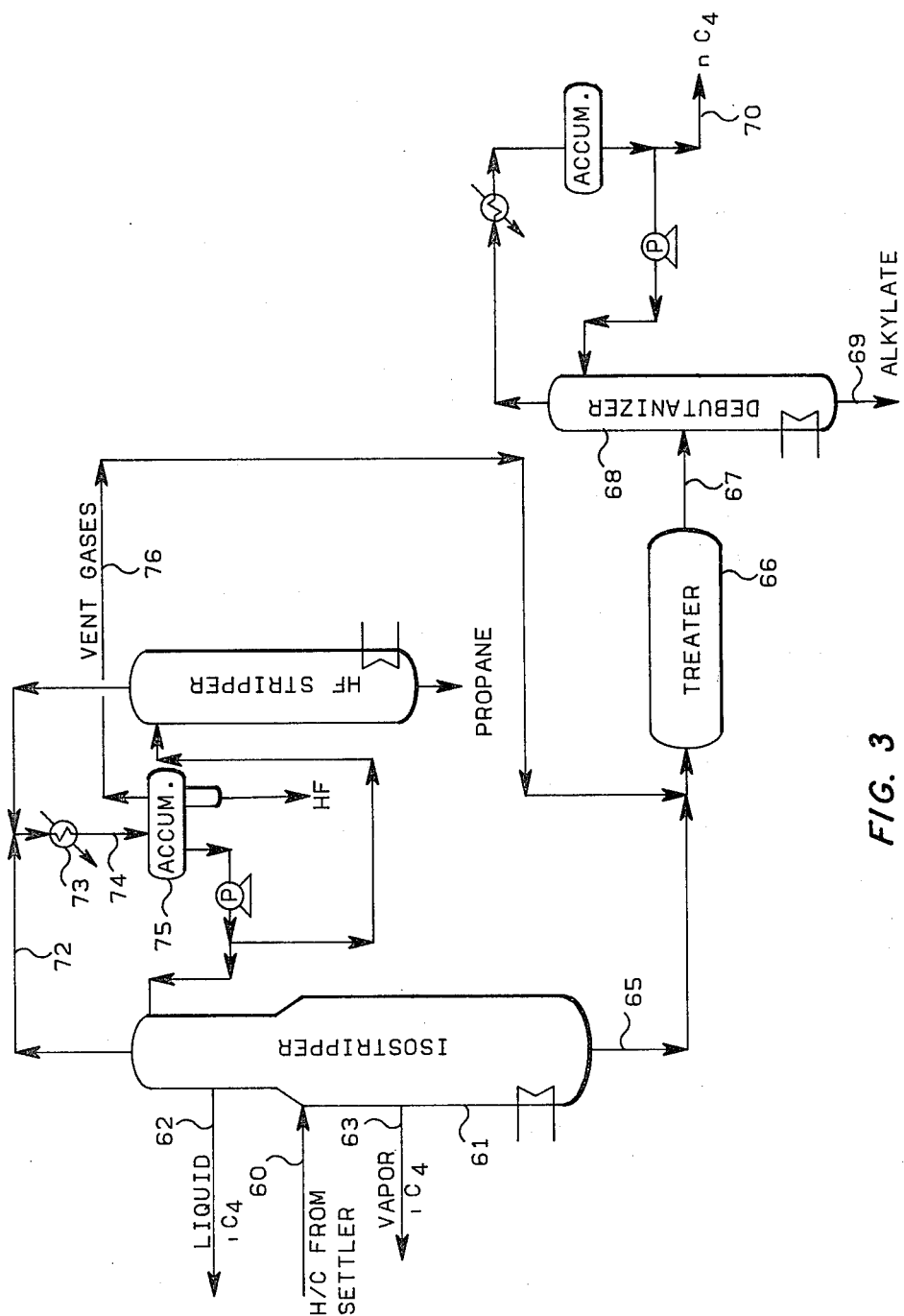
In FIG. 3, there is shown the combining of the vent gases with the bottoms of an isostripper which contain alkylate and normal butane prior to treating said bottoms, later separated, after treatment, into a normal butane stream and an alkylate stream.

FIGS. 2 and 3 are embodiments using an isostripper. In FIG. 2 the vent gases are treated with the normal butane removed as a side-draw from the isostripper. In FIG. 3, normal butane is recovered in the alkylate bottoms from the isostripper and vent gases are admixed therewith and charged to a treater. The mass is then passed to a debutanizing column and the propane is recovered in the normal butane.

From the foregoing description and that which follows it can be seen that the invention eliminates separate treating, e.g., caustic wash of vent gases and also that it recovers valuable propane yielded in the normal butane for example, in a liquified petroleum gas.

Referring now to FIG. 1, feed olefin and isobutane introduced at 1 is passed to riser reactor 2 together with recycle isobutane from 3 and with HF catalyst from 4 by way of cooler 5. The reacted admixture is passed from the reactor 2 to settler 6 in which an HF phase which settles is recirculated to the reactor by 4 and from which a supernatant hydrocarbon phase is taken off at 7 and pumped by 8 in part by 9 to depropanizer 10. Another part of the hydrocarbon phase is passed by 11 to deisobutanizer 12. Overhead from deisobutanizer 12 is in part used as reflux introduced to tower 12 at 13, the remainder being passed by 14 and 3 to reactor 2. Bottoms withdrawn from deisobutanizer 12 at 16 constitute alkylate and normal butane which is treated in treaters 17 and 18 to remove HF therefrom with, say, bauxite, following which it is debutanized in debutanizer 20 to produce debutanized alkylate at 21 and a normal butane stream at 22.

According to the invention, upon separation the vent gases, produced by passing depropanizer overhead containing propane and HF by 30 through cooler condenser 31 into accumulator 32, are passed by 35 to admixture with alkylate and normal butane in 16 prior to entry of stream 16 into treater 17.

It can be seen that the normal butane stream 22 will contain the propane contained originally in vent gases taken from accumulator 32 at 35.

Referring now to FIG. 2, hydrocarbon phase from an alkylation reaction effluent settler is passed by 40 into isostripper 41 from which alkylate is withdrawn at 42. Isobutane is removed as a liquid at 43 and recycled to the alkylation reaction.

A normal butane vapor sidedraw 44 is passed by cooler 45 and 46 and/or by 47 to treater 48 and removed from the operation at 49. Vent gases 50 produced from isostripper overhead 51 by way of cooler condenser 52 and accumulator 53, are passed into admixture with the normal butane side stream 44 removed from the isostripper 41 prior to entry of the stream into treater 48.

Referring now to FIG. 3, hydrocarbon phase from an alkylation effluent settler is passed by 60 into isostripper 61 from which there are removed a liquid stream 62 and a vapor stream 63. These streams are constituted substantially by isobutane and are returned to the alkylation reaction.

Bottoms from isostripper which contain alkylate and normal butane are withdrawn at 65 passed through treater 66 and by way of 67 passed to debutanizer 68 in which debutanized alkylate is produced and removed at 69. A normal butane stream is obtained as an overhead and taken off at 70.

Overhead 72 from the isostripper is cooled and condensed at 73 and passed by 74 into accumulator 75. Vent gases containing propane and HF are passed by 76 into admixture with isostripper bottoms of 65 before these enter treater 66.

It will be seen that in the modification of this figure as in the earlier described modification the HF into vent gases has been treated out therefrom and the propane advantageously recovered in the normal butane stream, as earlier described in more detail and with advantages also earlier described.

The following is a typical calculated example of operation related primarily to the embodiment of FIG. 1.

| HF Alkylation: | | |
| --- | --- | --- |
| Temperature, °F., | | 90 |
| Pressure, | | (to maintain liquid) |
| Total IC$_4$/Olefin (50-50 C$_3$=, C$_4$='s by Vol.) | | 10:1 |
| HF/Total H/C Vol Ratio | | 4:1 |
| Depropanizer: | | |
| Temperatures, °F., | | |
| Top, | | 122 |
| Bottom, | | 215 |
| Pressure, PSIA, | | 273 |
| HF Stripper: | | |
| Temperatures, °F., | | |
| Top, | | 120 |
| Bottom, | | 134 |
| Pressure, PSIA, | | 263 |
| Deisobutanizer: | | |
| Temperatures, °F. | | |
| Top, | | 130 |
| Bottom, | | 300 |
| Pressure, PSIA, | | 120 |
| Treaters: | | |
| Bauxite Used Vol H/C/Vol Bauxite/Hr., | | 0.5 |
| Debutanizer: | | |
| Temperature, °F., | | |
| Top, | | 160 |
| Bottom, | | 350 |
| Pressure, PSIA, | | 120 |
| Vent Gases (35) from Accumulator (32): | | |
| SCF/Day, | | 1.8 × 10$^6$ |
| Composition, Wt. % | Typical | |
| HF 1-10 | 5 | |
| Propane, 70-80 | 75 | |
| Ethane 10-30 | 20 | |
| Deisobutanized Alkylate (16): | | |
| (a) BBL/Hr., | | 500 |
| (a) Contains nC$_4$, BBL/Hr., | | 30-50 40 Typical |
| Normal Butane Yield (22): | | |
| (b) BBL/Hr., | | 41-42 Typical |
| HF, | | NIL |
| (b) Contains about 1 to 2 B/H Propane-Ethane | | |

Reasonable variation and modification are possible within the scope of the foregoing description, drawings, and the appended claims to the invention the essence of which is that an overhead of vent gases as obtained from a fractionator, e.g., a depropanizer and/or an isostripper, said overhead containing HF and propane, is advantageously admixed with another stream in the operation prior to treatment of said stream to remove HF therefrom, e.g., as with an alkylate before or after it has been debutanized and/or with a normal butane stream before it has been treated to remove HF therefrom.

We claim:

1. A process for improved recovery of HF and propane contained in vent gases resulting from an alkylation of hydrocarbons in the presence of HF under conditions to produce an alkylation effluent from which an alkylate product is recovered by fractionation thus producing an alkylate-containing stream which is treated to remove therefrom HF and a normal butane-containing stream which is recovered downstream of said treatment, which comprises introducing said vent gases into a stream in said fractionation prior to said treatment, thus recovering said propane in said normal butane-containing stream.

2. A process according to claim 1 wherein said alkylation effluent is depropanized and vent gases thus obtained containing HF and propane are admixed with said alkylate-containing stream prior to said treatment to remove HF therefrom.

3. A process according to claim 1 wherein the alkylate-containing stream is fractionated to remove alkylate therefrom and to generate a stream containing normal butane and said vent gases are admixed with said stream containing normal butane prior to a treatment thereof to remove HF therefrom.

4. A process according to claim 1 wherein the alkylate-containing stream is treated to remove HF therefrom, the vent gases are admixed with said alkylate containing stream prior to said treatment and wherein the treated alkylate containing stream is fractionated to produce a normal butane containing stream containing propane which was in said vent gases.

* * * * *